US011465953B2

(12) United States Patent
Tang et al.

(10) Patent No.: US 11,465,953 B2
(45) Date of Patent: Oct. 11, 2022

(54) METHOD FOR PURIFICATION OF A SOLVENT FOR SEPARATION OF STYRENE BY EXTRACTIVE DISTILLATION AND FOR SEPARATION OF STYRENE

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Wencheng Tang, Beijing (CN); Longsheng Tian, Beijing (CN); Ming Zhao, Beijing (CN); Siliang Gao, Beijing (CN); Nan Yang, Beijing (CN); Siyuan Qie, Beijing (CN); Zhifeng Bian, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 174 days.

(21) Appl. No.: 16/961,623

(22) PCT Filed: Jan. 9, 2019

(86) PCT No.: PCT/CN2019/070941
§ 371 (c)(1),
(2) Date: Jul. 10, 2020

(87) PCT Pub. No.: WO2019/137383
PCT Pub. Date: Jul. 18, 2019

(65) Prior Publication Data
US 2020/0354292 A1 Nov. 12, 2020

(30) Foreign Application Priority Data

Jan. 12, 2018 (CN) .......................... 201810030657.0

(51) Int. Cl.
*C07C 7/00* (2006.01)
*C07C 7/08* (2006.01)
(Continued)

(52) U.S. Cl.
CPC .............. *C07C 7/005* (2013.01); *B01D 1/065* (2013.01); *B01D 3/10* (2013.01); *B01D 3/148* (2013.01);
(Continued)

(58) Field of Classification Search
CPC .......... B01D 1/065; B01D 3/10; B01D 3/148; B01D 3/40; B01D 11/0488; C07C 7/005; C07C 7/08; C07C 7/10
See application file for complete search history.

(56) References Cited

U.S. PATENT DOCUMENTS 4,596,655 A * 6/1986 van Eijl .................... C07C 7/05
208/348
2011/0015460 A1* 1/2011 Ding ...................... C10G 21/28
585/806

FOREIGN PATENT DOCUMENTS

CN 101875592 A * 11/2010 ............... C07C 7/08
CN 101875592 A 11/2010
(Continued)

OTHER PUBLICATIONS

CN-104744206-A_English Translation (Year: 2015).*
CN-101875592-A_English Translation (Year: 2010).*
CN-103657121-A_English Translation (Year: 2012).*

*Primary Examiner* — Youngsul Jeong
(74) *Attorney, Agent, or Firm* — Novick, Kim & Lee, PLLC; Allen Xue

(57) ABSTRACT

A method for purification of a styrene-containing feedstock includes steps of introducing the styrene-containing feed-
(Continued)

stock into the middle of an extractive distillation column, and a solvent for the extractive distillation into the upper part of the column; discharging a raffinate oil from the top of the column, and a rich solvent rich in styrene from the bottom of the column. The rich solvent is then introduced into the middle of the solvent recovery column for vacuum distillation to obtain a crude styrene from the top of the solvent recovery column, and a lean solvent is discharged from the bottom of the solvent recovery column and recycled to the upper part of the extractive distillation column. A portion of the rich solvent is sent to a solvent purification zone for a liquid-liquid extraction using water to obtain a mixture of a styrene polymer and styrene.

23 Claims, 3 Drawing Sheets

(51) Int. Cl.
*B01D 1/06* (2006.01)
*B01D 3/10* (2006.01)
*B01D 3/14* (2006.01)
*B01D 3/40* (2006.01)
*B01D 11/04* (2006.01)
*C07C 7/10* (2006.01)

(52) U.S. Cl.
CPC ............ *B01D 3/40* (2013.01); *B01D 11/0488* (2013.01); *C07C 7/08* (2013.01); *C07C 7/10* (2013.01)

(56) References Cited

FOREIGN PATENT DOCUMENTS

| | | | | |
|---|---|---|---|---|
| CN | 101955410 A | | 1/2011 | |
| CN | 102452891 A | | 5/2012 | |
| CN | 103657121 A | * | 3/2014 | ............... B01D 1/22 |
| CN | 103657121 A | | 3/2014 | |
| CN | 104744206 A | * | 7/2015 | ............. C07C 15/46 |
| CN | 104744206 A | | 7/2015 | |
| WO | 2011008342 A1 | | 1/2011 | |

* cited by examiner

METHOD FOR PURIFICATION OF A SOLVENT FOR SEPARATION OF STYRENE BY EXTRACTIVE DISTILLATION AND FOR SEPARATION OF STYRENE

TECHNICAL FIELD

The present invention relates to a method for purification of a solvent for an extractive distillation, in particular to a method for purification of a solvent for separation of styrene by an extractive distillation and for separation of styrene.

BACKGROUND OF THE TECHNOLOGY

Styrene monomers are significant organic chemical raw materials, which are widely applied in plastics, coatings, pesticides, medicine, etc. The recovery of styrene products from styrene-containing feedstock oils via an extractive distillation process generates good economic benefits. Styrene monomers are easy to polymerize. In practical applications, despite of the addition of a polymerization inhibitor, the polymerization inhibitor can only reduce the extent of styrene polymerization, and it is impossible to completely avoid styrene polymerization. The boiling point of a styrene polymer is over 300° C., which is much higher than the boiling points of the components in feedstock oils. In the process of extractive distillation, the polymer is dissolved in the solvent system. Therefore, how to avoid the accumulation of the styrene polymer in the solvent and its further influence on the solvent performance is the key to ensure the long-term operation of styrene recovery device. The styrene polymer has a variety of components with a wide distillation range. The steam stripping regeneration method in the traditional process of extractive distillation of aromatics can only remove the polymers having much higher boiling points than the solvent. The low molecular polymer having a boiling point close to the solvent cannot be effectively removed by vacuum stripping.

CN101875592B discloses a regeneration method of the extracting solvent for extractive distillation of styrene. In this method, a lean solvent is back-extracted with a purifying agent and water to remove the styrene polymer in the solvent. Said employed purifying agent is $C_5$-$C_9$ alkanes or $C_6$-$C_9$ aromatics. After purification, the purifying agent rich in a styrene polymer is to enter a separate purifying agent recovery column to separate the purifying agent and the styrene polymer. The separated purifying agent is recycled and the styrene polymer is discharged from the system.

CN101955410A discloses a process and system for recovering styrene from a styrene-containing feedstock. In this method, a part of a lean solvent flow is treated with an organic solvent. Preferably the lean solvent flow is washed with water, and treated with a liquid-liquid equilibrium system of at least one equilibrium stage. The styrene polymer in the lean solvent is back-extracted into the organic solvent. Thus, the solvent system is purified, and the polymer-containing organic solvent is discharged.

The hydrocarbon phase of the purifying agent containing the polymer in the above-mentioned methods needs further treatment. The separation of the purifying agent and the polymer increases the operation steps and the separation equipment. The purification effect of the solvent and the difficulty of subsequent treatment also vary according to the performance of the purifying agent.

CONTENTS OF THE INVENTION

The object of the present invention is to provide a method for purification of a solvent for separation of styrene by an extractive distillation and a method for separation of styrene by an extractive distillation using the method. Said method can effectively remove the styrene polymer in the solvent for an extractive distillation, simplify the steps for the treatment of the solvent purifying agent, ensure the extractive distillation performance of the solvent, and extend the stable operation time of the device.

The method for purification of a solvent for separation of styrene by an extractive distillation provided by the present invention comprises following steps:

(1) a styrene-containing feedstock is introduced into an extractive distillation column from the middle, and a solvent for an extractive distillation is introduced into the extractive distillation column from an upper part; after an extractive distillation, a raffinate oil is discharged from the top of the extractive distillation column, and a rich solvent rich in styrene is discharged from the bottom of the column;

(2) the rich solvent described in the step (1) is introduced into a solvent recovery column from the middle; after vacuum distillation, a crude styrene is discharged from the top of the solvent recovery column, and a lean solvent is discharged from the bottom of the solvent recovery column and recycled to the upper part of the extractive distillation column;

(3) a part of the rich solvent described in the step (1) is separated and sent to a solvent purification zone where water is introduced; after a liquid-liquid extraction, a mixture of a styrene polymer and styrene is discharged from the top of the solvent purification zone, and the purified solvent containing water is discharged from the bottom of the solvent purification zone.

The method of the present invention can effectively remove the styrene polymer in the solvent by purifying the rich solvent discharged from the bottom of the extractive distillation column with styrene as a purifying agent. It can be combined with a subsequent styrene refining system to separate the styrene polymer and the purifying agent in the styrene refining process, thereby saving additional devices and simplifying the operation steps.

SPECIFIC EMBODIMENTS

Figure 1:
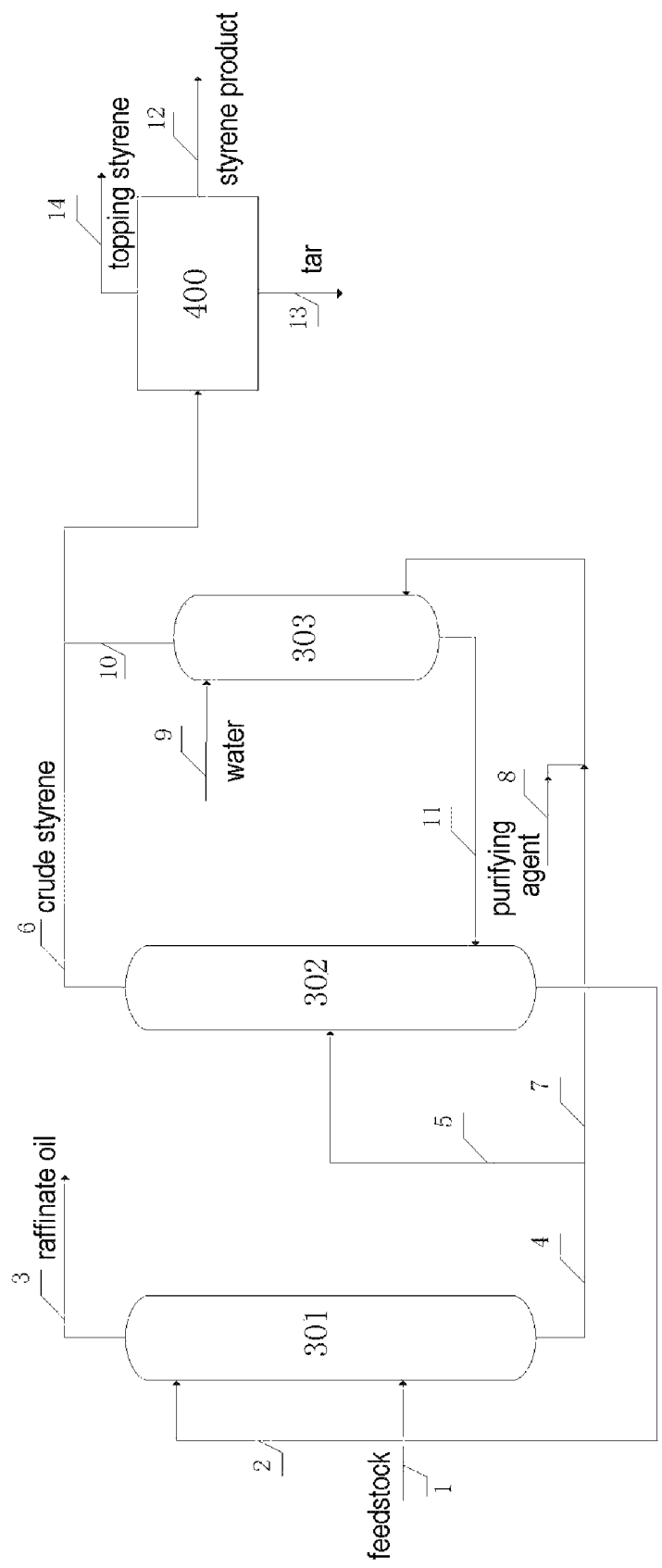
FIG. 1 is a flow diagram of purification treatment of a part of the rich solvent in the process of separation of styrene by an extractive distillation provided by the present invention.

The method of the invention can effectively remove the styrene polymer in the solvent, in particular the styrene oligomers (the low molecular polymers), by purifying a part of the rich solvent discharged from the bottom of the extractive distillation column with styrene as a purifying agent. Compared with the method of purification treatment of the lean solvent with a raffinate oil as a purifying agent, the use of styrene as a purifying agent can increase the solubility of the styrene polymer, reduce the emulsification in the purification process, and improve the efficiency of removing the styrene polymer in the solvent. Moreover, the rich solvent to be purified can be purified without entering the solvent recovery column, which can avoid further polymerization of the styrene polymer at a higher temperature in the solvent recovery column. More importantly, it is not necessary to recover the purifying agent separately. Instead, the recovery of the purifying agent and the refining of styrene can be combined in one step, where the styrene and the styrene polymer are separated in the styrene refining process. Thus, the operation steps are simplified without additional devices for recovering the purifying agent, and the energy consumption in the solvent purification process is reduced. The method of the invention can effectively remove the styrene polymer produced in the process of separating styrene by an extractive distillation, keep the performance of the solvent, and maintain the long-term operation of the device.

In the method of the invention, it is preferred to introduce a solvent purifying agent into the solvent purification zone described in the step (3). The solvent purifying agent comprises styrene and optional alkylaromatics, wherein the content of styrene is not less than 98% by mass, preferably not less than 99% by mass. The solvent purifying agent can be selected from the crude styrene discharged from the top of the solvent recovery column or a topping styrene discharged from the top of the styrene refining column.

In the solvent purification zone described in the step (3), the styrene polymer in the rich solvent to be purified is dissolved in styrene. The solvent is dissolved in water to form an oil phase and a water phase. The styrene polymer can be separated from the solvent upon separation of the oil phase and the water phase. In the step (3), the temperature of the solvent purification zone shall be controlled to prevent a styrene polymerization. The temperature of the solvent purification zone shall enable the styrene polymerization loss in the solvent purification process to be reduced to a negligible extent. The temperature of the solvent purification zone may be 20-65° C., preferably 30-60° C.; the pressure is 0.2-0.8 MPa, preferably 0.3-0.7 MPa.

A multi-stage liquid-liquid equilibrium treatment can be adopted for the liquid-liquid extraction performed in the solvent purification zone, and the number of the theoretical stage of the multi-stage liquid-liquid equilibrium treatment is preferably 2-10.

Said step (3) separates a part of the rich solvent for purification. The mass ratio of the separated rich solvent introduced into the solvent purification zone to the total amount of the rich solvent may be 0.5-20%, preferably 1-15%. The mass ratio of the water introduced into the solvent purification zone to the rich solvent introduced into the solvent purification zone may be 0.2-2.0, preferably 0.5-1.5. The mass ratio of the solvent purifying agent introduced into the solvent purification zone to the rich solvent introduced into the solvent purification zone may be 0.05-0.5, preferably 0.05-0.3.

Preferably, a mixture of styrene polymer and styrene discharged from the top of the solvent purification zone is sent to a styrene refining and treatment system to obtain a refined styrene product, a topping styrene and a polymer-rich tar.

Preferably, a part of the lean solvent discharged from the bottom of the solvent recovery column is separated and sent to a solvent regeneration column for a steam stripping regeneration. The regenerated solvent obtained after stripping is reused while the tar which cannot be stripped is discharged from the system. The reboiler of the solvent regeneration column is preferably a falling film evaporator placed outside the column.

The present invention also provides a method for separation of styrene by an extractive distillation from a styrene-containing feedstock, comprising following steps:

(1) a styrene-containing feedstock is introduced from the middle of an extractive distillation column; a solvent for an extractive distillation is introduced from an upper part of the extractive distillation column; after an extractive distillation, a raffinate oil is discharged from the top of the extractive distillation column, and a rich solvent rich in styrene is discharged from the bottom of the column;

(2) the rich solvent described in the step (1) is introduced into a solvent recovery column for vacuum distillation; a crude styrene which is discharged from the top of the solvent recovery column enters a styrene refining system; after drying and decolorizing treatment, the crude styrene enters a styrene refining column; a lean solvent is discharged from the bottom of the solvent recovery column;

(3) a part of the rich solvent described in the step (1) is separated and sent to a lower part of a solvent purification zone, and water is introduced to an upper part of the solvent purification zone; after a liquid-liquid extraction, a mixture of a styrene polymer and styrene is discharged from the top of the solvent purification zone; the purified solvent containing water is discharged from the bottom of the solvent purification zone;

(4) a stream discharged from the top of the solvent purification zone is introduced into the styrene refining system and then into the styrene refining column after drying and decolorizing;

(5) in the styrene refining column, a topping styrene is obtained at the top of the column after distillation; a refined styrene product is discharged from an upper part of the column, and a tar rich in polymer is discharged from the bottom of the column.

In the above step (3), the temperature of the solvent purification zone shall be controlled to prevent a styrene polymerization. The temperature of the solvent purification zone shall enable the styrene polymerization loss in the solvent purification process to be reduced to a negligible extent. The temperature of the solvent purification zone may be 20-65° C., preferably 30-60° C.; the pressure is 0.2-0.8 MPa, preferably 0.3-0.7 MPa.

In the above step (3), it is preferred to introduce a solvent purifying agent into the solvent purification zone. Said solvent purifying agent is preferably a crude styrene or the topping styrene discharged from the top of the styrene refining column.

The mass ratio of the separated rich solvent sent to the solvent purification zone in the step (3) to the total amount of the rich solvent may be 0.5-20%, preferably 1-15%. The mass ratio of water introduced into the solvent purification zone to the rich solvent entering the solvent purification zone may be 0.2-2.0, preferably 0.5-1.5. The mass ratio of the solvent purifying agent introduced into the solvent purification zone to the rich solvent introduced into the solvent purification zone may be 0.05-0.5, preferably 0.05-0.3.

Preferably, a part of the lean solvent obtained from the bottom of the solvent recovery column in step (2) is separated and sent to the solvent regeneration column for a steam stripping distillation regeneration. That is, heavy components in the solvent are removed by stripping. The vapor phase discharged from the top of the regeneration column returns to the lower part of the solvent recovery column, and the tar is discharged from the bottom of the solvent regeneration column.

The stripping temperature for regeneration of a part of the lean solvent as separated in the method of the present invention may be 110-150° C., and the pressure may be 10-30 kPa. Specifically, the pressure of the lean solvent regeneration column may be 10-30 kPa; the temperature is 110-150° C., preferably 130-150° C. The mass ratio of the steam to the lean solvent is preferably 3-8.

The mass ratio of the lean solvent for regeneration to the total amount of the lean solvent in the method may be 0.5-10%, preferably 0.5-5%.

After regeneration of the lean solvent by stripping, it returns to the bottom of the solvent recovery column in form of a vapor phase and acts as the stripping steam of the recovery column. The regeneration process is free of condensation and no additional energy consumption is needed.

Preferably, the reboiler of the solvent regeneration column is a falling film evaporator placed outside the solvent regeneration column. The falling film evaporator comprises a shell and heat exchange tubes placed in the shell. The upper end or one side of the shell is provided with a head which evenly distributes materials flowing into the heat exchange tubes. When used, the heating medium heats the heat exchange tubes in the shell by going through the shell of the falling film evaporator, i.e. through the shell side. The lean solvent to be regenerated enters the heat exchange tubes of the falling film evaporator (through the tube side) for a falling film evaporation. In the heat exchange tubes of the falling film evaporator, the lean solvent flows along the tube wall to form a liquid film. The lean solvent which evaporates on the liquid film becomes a vapor phase, while the liquid film flows downward under the action of gravity. Thus, the falling film evaporation is formed.

The present invention preferably adopts the regeneration method of combination of purification treatment of a rich solvent and steam stripping distillation of a lean solvent. Compared with the method of purification treatment of only the rich solvent, the method can reduce the treatment amount of the rich solvent relatively while maintaining the same polymer content in the solvent. Thus, the energy consumption can be reduced. In addition, the two regeneration methods are complementary. The steam stripping distillation regeneration of the lean solvent can remove the styrene high polymer (polymer with high molecular) and the solvent degradation products but cannot effectively remove styrene oligomers. Whereas the purification treatment of the rich solvent can effectively remove the styrene polymer, but cannot remove water-soluble solvent degradation products. In the practical application, the presence of active oxygen in the system can accelerate the degradation of the solvent. Therefore, the combined solvent regeneration method can effectively remove impurities in the solvent, keep the extractive distillation performance of the solvent, and maintain the long-term operation of the device.

In the method of the present invention, the pressure at the top of the extractive distillation column, the solvent recovery column and the styrene refining column may be 8-20 kPa; the temperature at the bottom of the extractive distillation column may be 110-145° C., and the theoretical plate number is preferably 30-60. The temperature at the bottom of the solvent recovery column may be 120-150° C., and the theoretical plate number is preferably 20-30. The temperature at the bottom of the styrene refining column may be 80-110° C., and the theoretical plate number is preferably 15-30.

In the present invention, the reflux ratio at the top of each of said columns is the mass ratio of the reflux amount of the material discharged from the top of the column into the upper part of the column to the material discharged from the top of the columne. The reflux ratio of the extractive distillation may be 1-3; the reflux ratio of the solvent recovery column may be 0.4-1.5, and the reflux ratio of the styrene refining column may be 1-3.

In the method of the present invention, the mass ratio of the solvent used for the extractive distillation to the feedstock may be 3-8, preferably 4-6. The solvent for the extractive distillation is preferably at least one selected from the group consisting of sulfolane, diethylene glycol, triethylene glycol, tetraethylene glycol, N,N-dimethylacetamide and N-formylmorpholine, more preferably sulfolane.

The feedstock according to the present invention is preferably a styrene-containing $C_8$ fraction, such as a $C_8$ fraction of pyrolysis gasoline, wherein the content of styrene is 20-70% by mass, and the balance is $C_8$ aromatics and non-aromatics.

The present invention is further illustrated in combination with the figures. Auxiliary equipments such as heat exchangers, reflux tanks and pumps are omitted in the figures. The person skilled in the art can understand the present invention according to the figures. The omission does not affect the specific enforcement.

In FIG. 1, the styrene-containing feedstock is introduced into the extractive distillation column 301 from the middle via line 1; a solvent for the extractive distillation is introduced into the upper part of the extractive distillation column 301 via line 2. After an extractive distillation, a raffinate oil free of styrene is discharged from line 3 at the top of the extractive distillation column. A rich solvent rich in styrene is discharged from the bottom of the extractive distillation column 301 through line 4 and separated into two parts, wherein a large part of the rich solvent enters the middle of the solvent recovery column 302 via line 5. Styrene is separated from the solvent for the extractive distillation by vacuum distillation. A crude styrene is discharged from line 6 at the top of the solvent recovery column. The lean solvent discharged from the bottom of the solvent recovery column is almost free of styrene. After a series of heat exchanges, the lean solvent is recycled to the upper part of the extractive distillation column 301 via line 2. A small part of the rich solvent as separated is sent to the solvent purification zone 303 via line 7 for treatment. In the solvent purification zone, an operation of a multi-stage liquid-liquid equilibrium can be performed, such as a multi-stage liquid-liquid extraction column. Preferably, a purifying agent is added to the solvent purification zone. Said purifying agent is introduced via line 8, mixed with the rich solvent in line 7, and then sent to the lower part of the solvent purification zone. Water is introduced to the solvent purification zone 303 from the upper part via line 9. After a liquid-liquid extraction, the styrene polymer is dissolved in styrene and discharged from line 10 at the top of the solvent purification zone. The solvent for the extractive distillation is dissolved with water and discharged from line 11 at the bottom of the solvent purification zone, and it is a purified solvent. The purified solvent is recycled to the lower part of the solve recovery column. The crude styrene discharged from line 6 and the polymer-containing purifying agent discharged from line 10 are mixed and then sent to a styrene refining treatment system 400. The styrene refining treatment system 400 includes dehydration, decolorization and a styrene refining column. The material entering the styrene refining treatment system is dried and decolorized before being sent to the styrene refining column. The refined styrene product is discharged from line 12 in upper part of the styrene refining column, the polymer-rich tar is continuously discharged from line 13 at the bottom of the styrene refining column, and a small amount of the topping styrene is discharged from line 14 at the top of the styrene refining column irregularly so as to enable the refined styrene product to reach the required purity.

Figure 2:
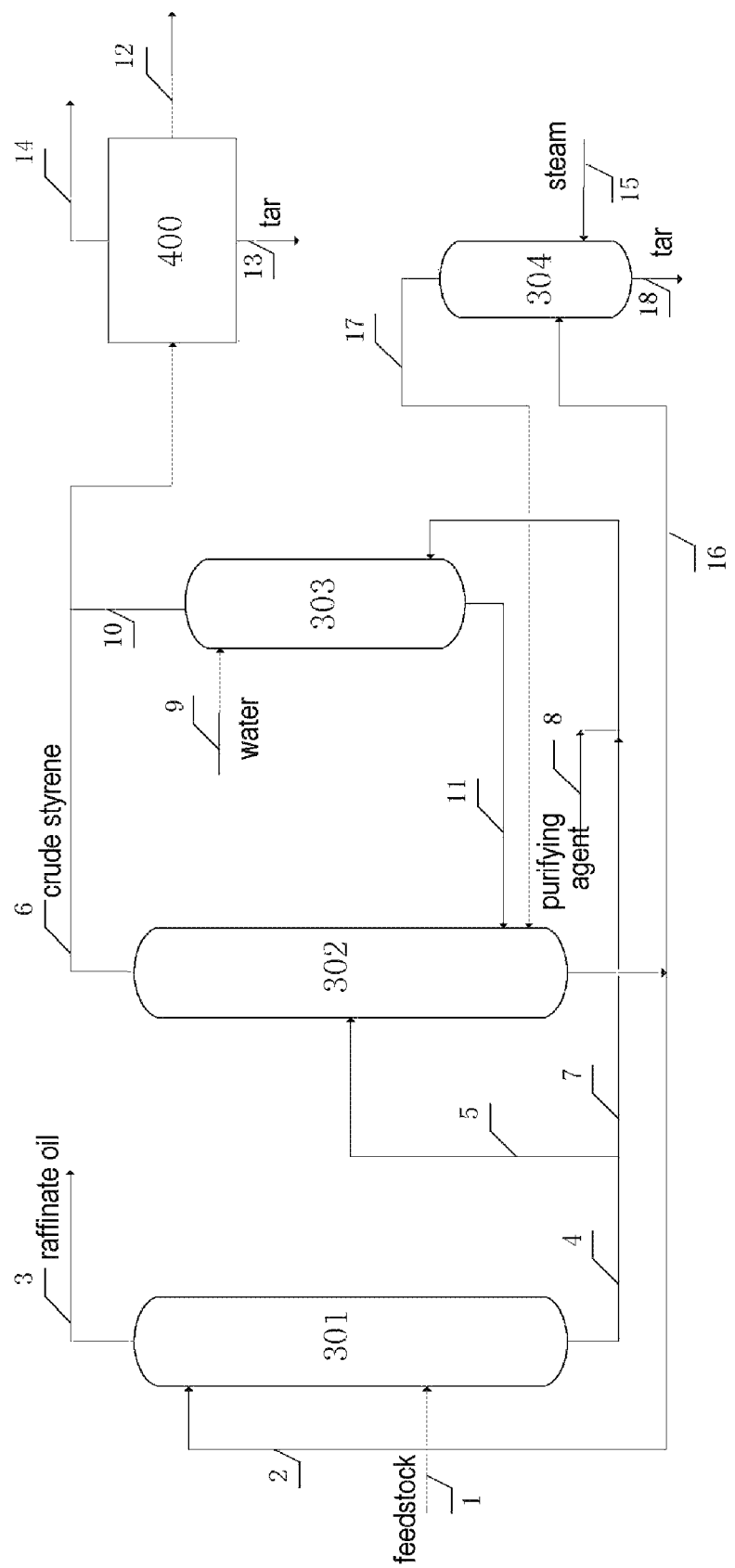
FIG. 2 is a flow diagram of purification treatment of a part of the rich solvent and steam stripping distillation treatment of a part of the lean solvent at the same time in the process of separation of styrene by an extractive distillation provided by the present invention.

The styrene recovery system shown in FIG. 2 is basically the same as that in FIG. 1, except for the addition of solvent regeneration column 304. The operation method is to separate the lean solvent discharged from the bottom of the solvent recovery column 302 into two parts, wherein a large part of the lean solvent is recycled to the upper part of the extractive distillation column 301 via line 2, while a small part of the lean solvent is introduced into the middle of the solvent regeneration column 304 via line 16. Steam is introduced into the lower part of the solvent regeneration column 304 via line 15. A reboiler (not shown in the figure) is provided at the bottom of the solvent regeneration column. After steam stripping, the regenerated solvent from which heavy components are removed is discharged along with the steam from line 17 at the top of the column and sent to the bottom of the solvent recovery column 302 and acts as the stripping steam of the solvent recovery column. Heavy component impurities including the styrene high polymer and the solvent degradation products at the bottom of the regeneration column are discharged via line 18.

Figure 3:
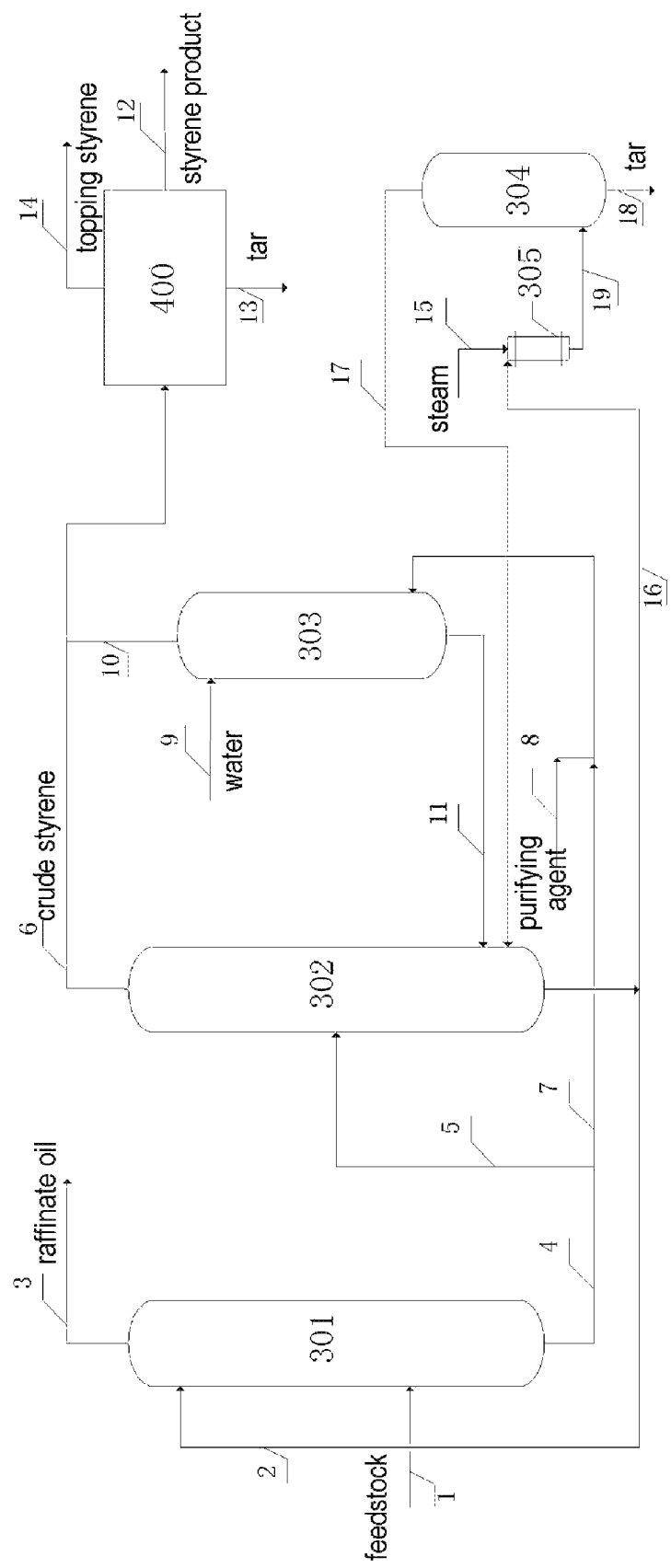
FIG. 3 is a flow diagram of purification treatment of a part of the rich solvent and steam stripping distillation treatment of a part of the lean solvent at the same time, and the use of a falling film evaporator as heater of the solvent regeneration column in the process of separation of styrene by an extractive distillation provided by the present invention.

The styrene recovery system shown in FIG. 3 is basically the same as that in FIG. 2 except for the use of a falling film evaporator 305 provided outside the solvent regeneration column 304 as the heater of the regeneration column 304. The operation method is to separate the lean solvent discharged from the bottom of the solvent recovery column 302 into two parts, wherein a large part of the lean solvent is recycled to the upper part of the extractive distillation column 301 via line 2, while a small part of the lean solvent is introduced to the falling film evaporator 305 via line 16. Steam is introduced into the falling film evaporator 305 from the top via line 15. In the falling film evaporator, a top-down flow of the lean solvent and the steam passes the heat exchange tubes of the falling film evaporator for a falling film evaporation. The shell side outside the heat exchange tubes of the falling film evaporator is a heating medium. The heated vapor-liquid mixture flows to the lower part of the solvent recovery column 304 by gravity via line 19. After an evaporation in vacuum, the regenerated solvent is discharged along with the steam from line 17 at the top of the column and sent to the bottom of the solvent recovery column 302 and acts as the stripping steam of the solvent recovery column. Heavy component impurities including the styrene high polymer and the solvent degradation products at the bottom of the regeneration column are discharged from line 18.

A traditional plug-in reboiler placed in a lean solvent regeneration column is replaced by a falling film evaporator, as eliminates the hydrostatic pressure during the heating process. There is no overheating section in the heat exchange tubes of the falling film evaporator, and the operating temperature of the heater can be reduced by 5-10° C. under the same operating pressure of the regeneration column, as can effectively prevent the high temperature polymerization of styrene and inhibit the scaling of the heat exchange tube wall, thereby prolonging the operation period of the device.

The present invention is further explained in details with the examples. However, the present invention is not limited by these examples.

Example 1

A $C_8$ fraction of the pyrolysis gasoline having a composition as shown in Table 1 is used as the feedstock. The feedstock was subjected to an extractive distillation according to the procedure of FIG. 1. Styrene therein was separated and recovered, and a small part of the rich solvent was purified. The employed solvent for the extractive distillation was sulfolane. The purifying agent was a crude styrene discharged from the top of the solvent recovery column, wherein the content of styrene is 99.5% by mass.

The theoretical plate number of the extractive distillation column 301 was 55; the reflux ratio at the top of the column was 2; the top pressure of the column was 13 kPa; the bottom temperature of the column was 130° C., and the mass ratio of the solvent to the feedstock was 4.5.

The theoretical plate number of the solvent recovery column 302 was 25; the top pressure of the column was 13 kPa; the reflux ratio at top of the column was 0.8, and the bottom temperature of the column was 140° C.

The rich solvent discharged from the bottom of the extractive distillation column was separated into two parts, where the large part was sent to the solvent recovery column while the small part was sent to the lower part of the solvent purification column 303. The theoretical plate number of the solvent purification column 303 was 4; the pressure at top of the column was 0.5 MPa; and the operating temperature was 50° C. The mass ratio of the rich solvent sent to the solvent purification column to the total amount of the rich solvent was 10%; the mass ratio of the purifying agent to the rich solvent sent to the solvent purification column was 0.2, and the mass ratio of water to the rich solvent sent to the solvent purification column was 1.0.

The material discharged from the solvent purification column was sent to the styrene refining system 400, dried and decolorized before being sent to the styrene refining column. The theoretical plate number of the styrene refining column was 20, the top pressure of the column was 10 kPa, the reflux ratio at top of the column was 2.0, and the bottom temperature of the column was 90° C. After distillation, the refined styrene was discharged from the upper part of the styrene refining column, the tar rich in styrene polymer was discharged from the bottom of the column, and a topping styrene was discharged from the top of the column irregularly.

Under the above operation conditions, the content of the styrene polymer in the solvent for the extractive distillation was maintained at 1.0% by mass. The device was operated continuously and stably. The purity of the resulting refined styrene product was 99.86% by mass, and the yield was 94% by mass. See Table 3 for the main operation conditions and the relative energy consumption per unit mass of the refined styrene product produced by the whole device.

Comparative Example 1

It uses a raffinate oil as a purifying agent to purify the lean solvent.

A $C_8$ fraction of the pyrolysis gasoline having a composition as shown in Table 1 was used as the feedstock. The $C_8$ fraction of the pyrolysis gasoline was subjected to an extractive distillation according to the procedure of FIG. 1 to separate and recover styrene. The solvent for the extractive distillation and the operation conditions for the extractive distillation column, the solvent recovery column, the solvent purification column and the styrene refining treatment system were the same as those in Example 1, except that the rich solvent discharged from the bottom of the extractive distillation column 301 was all sent to the solvent recovery column 302, and then the lean solvent discharged from the bottom of the solvent recovery column was separated into two parts, wherein the large part returned to the upper part of the extractive distillation column via line 2, while the small part of the lean solvent was sent to the lower part of the solvent purification column 303 for purification. The location to which the lean solvent was sent was the same as the location to which the rich solvent was sent for purification in Example 1. The purifying agent was the raffinate oil discharged from the top of the extractive distribution column, and see Table 2 for its composition. In addition, another purifying agent recovery column was added, and this column is connected with the line at the top of the solvent purification column.

The lean solvent after purification treatment contained a large amount of water and a trace of $C_8$ aromatics. After stripping a part of water and $C_8$ aromatics by heating, the lean solvent was recycled to the bottom of the solvent recovery column 302. A mixture of the purifying agent and the styrene polymer discharged from the top of the solvent purification column 303 reentered the newly-added purifying agent recovery column (not shown). The theoretical plate number of this purifying agent recovery column was 15; the top pressure of the column was 15 kPa; the reflux ratio at the top of the column was 0.3, and the bottom temperature of the column was 120° C. The purifying agent distilled from the purifying agent recovery column could be reused or added to the raffinate oil product while the styrene polymer-containing tar was discharged from the bottom of the column.

In the above operation process, the mass ratio of the lean solvent that was purified to the total amount of the lean solvent was 10%; and the mass ratio of water to the lean solvent that was purified was 1.0. In order to achieve the same effect of removing the styrene polymer as in Example 1, the styrene polymer content in the lean solvent was maintained at 1.0% by mass, and the mass ratio of the purifying agent to the lean solvent that was purified was increased to 0.5

Under the above operation conditions, the device was operated continuously and stably. The purity of the resulting refined styrene product was 99.86% by mass, and the yield was 94% by mass. See Table 3 for the main operation conditions and the relative value of energy consumption per unit product.

Compared with Example 1, Comparative Example 1 needs an additional purifying agent recovery column. Both the operation steps and the device investment increase, and the amount of the purifying agent in Comparative Example 1 is increased by 1.5 times as high as that of Example 1. The energy consumption for the portion of the solvent purification in Comparative Example 1 is increased by about 150% compared with Example 1. The energy consumption per unit product produced by the whole device is increased by about 3% compared with Example 1.

Example 2

A $C_8$ fraction of the pyrolysis gasoline having a composition as shown in Table 1 was used as the feedstock. The $C_8$ fraction of the pyrolysis gasoline was subjected to an extractive distillation according to the procedure of FIG. 2 to separate and recover styrene. In the operating process, a small part of the rich solvent was purified and a small part of the lean solvent was regenerated by steam stripping at the same time. The employed solvent for the extractive distillation, the purifying agent and the operation conditions for the extractive distillation column, the solvent recovery column, the solvent purification column and the styrene refining treatment system were all the same as those in Example 1.

The lean solvent discharged from the bottom of the solvent recovery column was separated into two parts, wherein the large part returned to the upper part of the extractive distillation column via line 2, while the small part of the lean solvent was sent to the solvent regeneration column 304 for regeneration by a steam stripping distillation. The mass ratio of the small part of the lean solvent for regeneration to the total amount of the lean solvent was 1%, and the mass ratio of the steam to the lean solvent for regeneration was 5. The solvent regeneration column 304 had a pressure of 20 kPa and a temperature of 145° C. The reboiler of the solvent regeneration column which was placed in the column kettle was a plug-in reboiler.

A small part of the rich solvent discharged from the bottom of the extractive distillation column was sent to the lower part of the solvent purification column 303. The mass ratio of the purifying agent to the rich solvent to be purified was 0.2, and the mass ratio of water to the rich solvent to be purified was 1.0. As the solvent regeneration column 304 had the function of removing the styrene high polymer in the solvent, the styrene polymer content in the lean solvent was maintained at 1.0% by mass, the treatment amount of the rich solvent to be purified was properly reduced, and the mass ratio of the rich solvent to be purified to the total amount of the rich solvent was 9% in order to achieve the same effect of removing the styrene polymer as in Example 1.

Under the above operation conditions, the styrene polymer content in the solvent for the extractive distillation was maintained at 1.0% by mass. The device was operated continuously and stably. The purity of the resulting refined styrene product was 99.86% by mass, and the yield was 94% by mass. See Table 3 for the main operation conditions and the relative energy consumption per unit mass of the refined styrene product produced by the whole device. See Table 4 for the temperature and the operation time of the reboiler of the solvent regeneration column.

Comparative Example 2

A $C_8$ fraction of the pyrolysis gasoline having a composition as shown in Table 1 was used as the feedstock. The $C_8$ fraction of the pyrolysis gasoline was subjected to an extractive distillation according to the procedure of FIG. 2 to separate and recover styrene, except that the lean solvent discharged from the bottom of the solvent recovery column was separated into two parts, wherein the large part returned to the upper part of the extractive distillation column via line 2, while the small part of the lean solvent was sent to the lower part of the solvent purification column 303 for purification. The location to which the lean solvent was sent was the same as the location to which the rich solvent was sent for purification in Example 2.

As the lean solvent was basically free of styrene, in order to achieve the same effect of removing the styrene polymer as in Example 1, the styrene polymer content in the lean solvent was maintained at 1.0% by mass; the mass ratio of the purifying agent to the solvent to be purified was increased to 0.3. The solvent for the extractive distillation, the purifying agent and the operation conditions for the extractive distillation column, the solvent recovery column, the solvent purification column and the styrene refining treatment system were all the same as in Example 2.

Under the above operation conditions, the styrene polymer content in the solvent for the extractive distillation was maintained at 1.0% by mass. The device was operated continuously and stably. The purity of the resulting refined styrene product was 99.86% by mass, and the yield was 94% by mass. See Table 3 for the main operation conditions and the relative energy consumption per unit mass of the refined styrene product produced by the whole device.

It can be seen from Table 3 that, compared with Example 2, the consumption of the purifying agent in Comparative Example 2 is increased by 50%; the energy consumption for the portion of the solvent purification and the regeneration is increased by 50% compared with Example 2, and the energy consumption per unit of the product of the whole device is increased by 1.2% compared with Example 2.

Example 3

A $C_8$ fraction of the pyrolysis gasoline having a composition as shown in Table 1 was used as the feedstock. The $C_8$ fraction of the pyrolysis gasoline was subjected to an extractive distillation according to the procedure of FIG. 3 to separate and recover styrene, wherein the rich solvent discharged from the bottom of the extractive distillation column was separated into two parts, wherein the large part was sent to the solvent recovery column, while the small part was sent to the lower part of the solvent purification column 303.

The lean solvent discharged from the bottom of the solvent recovery column was separated into two parts, wherein the large part returned to the upper part of the extractive distillation column via line 2 while the small part of lean solvent was sent to the upper part of the falling film evaporator 305. Steam was introduced from the top of the falling film evaporator 305. A top-down flow of the lean solvent and the steam passed through the heat exchange tubes of the falling film evaporator for a falling film evaporation. The heating medium of the shell side outside the heat exchange tubes of the falling film evaporator was steam. The material subjected to the falling film evaporation flew to the lower part of the solvent recovery column 304 by gravity. After evaporation in vacuum, the regenerated solvent along with the steam was discharged from the line 17 at the top of the column and sent to the bottom of the solvent recovery column 302 and acts as a stripping steam of the solvent recovery column. Heavy component impurities including the styrene high polymer and the solvent degradation products at the bottom of the regeneration column were discharged from line 18. The mass ratio of the regenerated lean solvent to the total amount of the lean solvent was 1%; the mass ratio of the steam to the regenerated lean solvent was 5. The pressure of the solvent regeneration column 304 was 20 kPa. The operation temperature of the falling film evaporator was 135° C. The other operation conditions for each of the columns, the solvent for the extractive distillation and the purifying agent were all the same as those of Example 2.

Under the above operation conditions, the styrene polymer content in the solvent for the extractive distillation was maintained at 1.0% by mass. The device was operated continuously and stably. The purity of the resulting refined styrene product was 99.86% by mass, and the yield was 94% by mass. See Table 3 for the main operation conditions and the relative energy consumption per unit mass of the refined styrene product produced by the whole device. See Table 4 for the temperature and the operation time of the falling film evaporator.

It can be seen from Table 4 that a falling film evaporator was used in the lean solvent regeneration column in Example 3 as a reboiler. Since there was no hydrostatic pressure in the falling film evaporator, the operation temperature was 10° C. lower than that of Example 2, as could reduce the styrene polymerization, thereby effectively reducing the scaling resulting from polymerization of styrene on the reboiler tube wall. The operation time was extended by 5 times.

TABLE 1

| components | content, % by mass |
|---|---|
| toluene | 0.1 |
| ethylbenzene | 15.5 |
| p-xylene | 8.8 |
| m-xylene | 20.0 |
| o-xylene | 11.9 |
| styrene | 38.1 |
| $C_9$ aromatics | 0.1 |
| non aromatics | 5.5 |

TABLE 2

| components | content, % by mass |
|---|---|
| toluene | 0.2 |
| ethylbenzene | 24.9 |
| p-xylene | 14.1 |
| m-xylene | 32.1 |
| o-xylene | 19.0 |
| styrene | 0.7 |
| $C_9$ aromatics | 0.1 |
| non aromatics | 8.9 |

TABLE 3

| item | Example 1 | Comparative Example 1 | Example 2 | Comparative Example 2 | Example 3 |
|---|---|---|---|---|---|
| purifying agent | crude styrene | raffinate oil | crude styrene | crude styrene | crude styrene |
| solvent to be purified | rich solvent | lean solvent | rich solvent | lean solvent | rich solvent |
| purifying solvent/total solvent, % by mass | 10 | 10 | 9 | 9 | 9 |
| water/purifying solvent mass ratio | 1.0 | 1.0 | 1.0 | 1.0 | 1.0 |

TABLE 3-continued

| item | Example 1 | Comparative Example 1 | Example 2 | Comparative Example 2 | Example 3 |
|---|---|---|---|---|---|
| purifying agent/purifying solvent mass ratio | 0.2 | 0.5 | 0.2 | 0.3 | 0.2 |
| steam stripping regeneration solvent | — | — | lean solvent | lean solvent | lean solvent |
| regenerated lean solvent/total lean solvent, % by mass | — | — | 1.0 | 1.0 | 1.0 |
| stripping steam/regenerated lean solvent, mass | — | — | 5 | 5 | 5 |
| polymer content in the lean solvent, % by mass | 1.0 | 1.0 | 1.0 | 1.0 | 1.0 |
| relative energy consumption of portion of solvent purification and regeneration, % | 110 | 277 | 100 | 150 | 100 |
| relative energy consumption per unit product of the whole device, % | 100.2 | 103.2 | 100.0 | 101.2 | 100.0 |
| number of purifying agent recovery column | 0 | 1 | 0 | 0 | 0 |

TABLE 4

| item | Example 2 | Example 3 |
|---|---|---|
| kind of the employed heater of the solvent regeneration column | plug-in type at the bottom of the regeneration column | falling film evaporator outside the regeneration column |
| reboiler temperature, ° C. | 145 | 135 |
| operation time of the heater of the solvent regeneration column, month | 2 | 12 |

It can be seen from Table 3 that, compared with Comparative Example 1, as Example 1 adopted a better purifying agent and purified the rich solvent so that the styrene in the rich solvent was recovered simultaneously during the purification process, the addition amount of the purifying agent was reduced by 60%, the energy consumption for the portion of solvent purification was reduced by about 60%, and the energy consumption per unit product produced for the whole device was reduced by about 3%. In addition, Example 1 does not need to set up a purifying agent recovery system separately, as simplifies the operation steps and reduces the equipment investment.

According to the comparison between Example 2 and Comparative Example 2 in Table 3, Example 2 selected a small part of the rich solvent for a purification treatment. Under the circumstance of the same effect of removing the polymer from the solvent for the extractive distillation, the purifying agent consumption in Example 2 is reduced by 33% compared with Comparative Example 2, the energy consumption for the portion of the solvent purification and regeneration is reduced by about 33%, and the energy consumption per unit product for the whole device is reduced by about 1%. Example 2 has better technical and economic indicators than Comparative Example 2.

It can be seen from Table 3, compared with Example 1, Example 2 uses the combination of the rich solvent purification and the lean solvent regeneration by steam stripping to maintain the quality of the solvent for the extractive distillation. From the perspective of energy consumption, the energy consumption of Example 2 is slightly reduced. Moreover, Example 2 can effectively remove water-soluble solvent degradation products by steam stripping. In the practical application, the presence of active oxygen in the system will accelerate the solvent degradation. Therefore, the use of the combined method of Example 2 allows synergistic effect between the rich solvent purification and the lean solvent regeneration by steam stripping and complementation to each other. Example 2 is more conducive to keep the performance of the solvent for the extractive distillation and maintain the long-term operation of the device.

It can be seen from Table 4 that the continuous operation time in the portion of the solvent regeneration in Example 3 is greatly prolonged owing to the use of a falling film evaporator. Thus, it is a better embodiment.

The invention claimed is:

1. A method for purification of a solvent for separation of styrene by extractive distillation, comprising:
   (1) feeding a styrene-containing feedstock into a middle part of an extractive distillation column and a solvent for extractive distillation into an upper part of the extractive distillation column to carry out extractive distillation;
   discharging a raffinate oil from a top of the extractive distillation column; and
   discharging a rich solvent rich in styrene from the from a bottom of the extractive distillation column;
   (2) feeding a first portion of the rich solvent into a solvent recovery column to carry out vacuum distillation;
   discharging a crude styrene from a top of the solvent recovery column;
   discharging a lean solvent from a bottom of the solvent recovery column;
   and feeding the lean solvent to the upper part of the extractive distillation column; and
   (3) feeding water and a second portion of the rich solvent into a solvent purification zone to carry out liquid-liquid extraction;
   discharging a mixture of a styrene polymer and styrene from a top of the solvent purification zone; and
   discharging a purified solvent containing water from a bottom of the solvent purification zone.

2. The method according to claim 1, further comprising feeding a solvent purifying agent into the solvent purification zone, said solvent purifying agent comprising not less than 98% by mass of styrene and optional alkylaromatics.

3. The method according to claim 2, wherein said solvent purifying agent is the crude styrene discharged from the top of the solvent recovery column or a topping styrene discharged from the top of a styrene refining column.

4. The method according to claim 1, wherein the solvent purification zone is at a temperature of 20-65° C. and a pressure of 0.2-0.8 MPa.

5. The method according to claim 4, wherein the temperature of the solvent purification zone is 30-60° C., and a number of equilibrium theoretical stage of the liquid-liquid extraction carried out in the solvent purification zone is 2-10.

6. The method according to claim 1, wherein a mass ratio of the second portion of the rich solvent fed into the solvent purification zone to a total amount of the rich solvent is 0.5-20%.

7. The method according to claim 1, wherein a mass ratio of the water fed into the solvent purification zone to the second portion of the rich solvent fed into the solvent purification zone is 0.2-2.0.

8. The method according to claim 2, wherein a mass ratio of the solvent purifying agent fed into the solvent purification zone to the second portion of the rich solvent is 0.05-0.5, and a mass ratio of the water to the second portion of the rich solvent is 0.2-2.0.

9. The method according to claim 1, further comprising:
feeding a mixture of the styrene polymer and the styrene discharged from the top of the solvent purification zone into a styrene refining system to obtain a refined styrene product, a topping styrene, and a polymer-rich tar.

10. The method according to claim 1, further comprising regenerating a portion of the lean solvent discharged from the bottom of the solvent recovery column in a solvent regeneration column by steam stripping to obtain a regenerated solvent and a tar.

11. The method according to claim 10, a mass ratio of the portion of the lean solvent to a total amount of the lean solvent is 0.5-10%.

12. The method according to claim 10, wherein the solvent regeneration column has a reboiler that is a falling film evaporator placed outside the solvent regeneration column.

13. The method according to claim 1, wherein the solvent for the extractive distillation is at least one selected from the group consisting of sulfolane, diethylene glycol, triethylene glycol, tetraethylene glycol, N,N-dimethylacetamide, and N-formylmorpholine.

14. The method according to claim 1, wherein the styrene-containing feedstock is a styrene-containing $C_8$ fraction.

15. A method for separation of styrene by an extractive distillation, comprising:
(1) feeding a styrene-containing feedstock into a middle part of an extractive distillation column and a solvent for an extractive distillation into an upper part of the extractive distillation column to carry out extractive distillation;
discharging a raffinate oil from a top of the extractive distillation column; and
discharging a rich solvent rich in styrene from a bottom of the extractive distillation column;
(2) feeding a first portion of the rich solvent into a solvent recovery column to carry out vacuum distillation;
discharging a crude styrene from a top of the solvent recovery column; and, after drying and decolorizing treatment, feeding the dried and discolorized crude styrene into a styrene refining column; and
discharging a lean solvent from a bottom of the solvent recovery column;
(3) feeding a second portion of the rich solvent into a lower part of a solvent purification zone and water into an upper part of the solvent purification zone to carry out liquid-liquid extraction;
discharging a mixture of a styrene polymer and styrene from a top of the solvent purification zone; and
discharging a purified solvent containing water from a bottom of the solvent purification zone;
(4) drying and discolorizing a stream discharged from the top of the solvent purification zone and then feeding the dried and discolorized stream into the styrene refining column; and
(5) discharging a topping styrene from a top of the styrene refining column after distillation, a refined styrene product from an upper part of the styrene refining column, and a tar rich in polymer from a bottom of the styrene refining column.

16. The method according to claim 15, feeding a solvent purifying agent into the solvent purification zone, wherein said solvent purifying agent is a crude styrene or the topping styrene discharged from the top of the styrene refining column.

17. The method according to claim 15, wherein the solvent purification zone is at a temperature of 20-65° C., and a pressure of 0.2-0.8 MPa.

18. The method according to claim 15, wherein a mass ratio of the second portion of the rich solvent fed into the solvent purification zone to a total amount of the rich solvent is 0.5-20%.

19. The method according to claim 15, wherein a mass ratio of the water fed into the solvent purification zone to the second portion of the rich solvent is 0.2-2.0.

20. The method according to claim 16, wherein a mass ratio of the solvent purifying agent fed into the solvent purification zone to the second portion of the rich solvent is 0.05-0.5, and a mass ratio of the water to the second portion of the rich solvent is 0.2-2.0.

21. The method according to claim 15, further comprising:
feeding a portion of the lean solvent into a solvent regeneration column to carry out steam stripping distillation;
returning a vapor phase discharged from a top of the solvent regeneration column to a lower part of the solvent recovery column; and discharging a tar from a bottom of the solvent regeneration column,
wherein the solvent regeneration column is at a pressure of 10-30 kPa, and a temperature is 110-150° C., and has a mass ratio of the steam to the lean solvent of 3-8.

22. The method according to claim 21, wherein a mass ratio of the lean solvent fed into the solvent regeneration column to a total amount of the lean solvent is 0.5-10%.

23. The method according to claim 21, wherein the solvent regeneration column has a reboiler that is a falling film evaporator placed outside the solvent regeneration column.

* * * * *